United States Patent [19]

Hakki

[11] Patent Number: 5,197,972
[45] Date of Patent: Mar. 30, 1993

[54] ARTERIAL MANOMETRIC DRESSING

[76] Inventor: A-Hamid Hakki, 2530 Gary Cir., No. 304, Dunedin, Fla. 34698-1770

[21] Appl. No.: 674,837

[22] Filed: Mar. 25, 1991

[51] Int. Cl.$^5$ ............................................ A61B 17/12
[52] U.S. Cl. ...................................... 606/201; 128/691
[58] Field of Search .............................. 606/201–206; 128/660.01, 660.04, 662.03, 661.08, 691, 660.02

[56] References Cited

U.S. PATENT DOCUMENTS

| | | | |
|---|---|---|---|
| 3,625,219 | 12/1971 | Abrams et al. | 606/203 |
| 3,779,249 | 12/1972 | Semlar | 606/201 |
| 4,154,231 | 5/1979 | Russell | 128/660.04 |
| 4,233,980 | 11/1980 | McRae et al. | 606/201 |
| 4,509,528 | 4/1985 | Sahota | 128/691 |
| 4,572,182 | 2/1986 | Royse | 606/201 |
| 4,579,123 | 4/1986 | Chen et al. | 128/662.03 |
| 4,677,853 | 7/1987 | Kawabuchi | 128/660.1 |
| 4,770,175 | 9/1988 | McEwen | 606/203 |
| 4,796,632 | 1/1989 | Boyd et al. | 128/662.03 |

Primary Examiner—C. Fred Rosenbaum
Assistant Examiner—William Lewis
Attorney, Agent, or Firm—Caesar, Rivise, Bernstein, Cohen & Pokotilow, Ltd.

[57] ABSTRACT

An arterial manometric dressing includes a pressure applying assembly having a pressure pad at a lower end thereof. A Doppler probe for determining blood flow in an artery forms part of the pressure applying assembly and engages an upper wall of the pressure pad, through which ultrasound signals are adapted to be transmitted. The pad also has a lower surface spaced from the upper surface for engaging a patient in a region for apply a pressure to an artery, and a fluid for transmitting ultrasound signals to and from the Doppler probe is disposed between the upper and lower walls of the pad. The dressing also employs a pressure indicating device for indicating the amount of pressure being applied to the artery. The invention also resides in the fluid-filled pressure pad, both alone and in combination with the Doppler probe.

9 Claims, 2 Drawing Sheets

ARTERIAL MANOMETRIC DRESSING

FIELD OF THE INVENTION

This invention relates generally to pressure applying devices usable in the medical field, and more specifically to an arterial dressing for use at an arterial puncture site after performance of an intra-arterial catheterization or similar procedure.

BACKGROUND ART

Traditionally arterial punctures have been managed by the application of manual pressure at the puncture site, immediately after withdrawal of the intra-arterial catheter. By applying such manual pressure a seal is formed, made up principally of blood elements, thereby preventing the undesired escape of blood from the artery.

Although the application of manual pressure to the area of an arterial puncture has proven satisfactory in many applications, such a procedure does have a number of drawbacks. First, the person apply such pressure often experiences undue hand and arm muscle fatigue. Second, since the pressure is applied manually it is difficult to maintain a constant and controlled pressure at the puncture site. This can result in the application of a pressure which is too high, thereby cutting off desired blood flow through the artery. Third, the use of skilled personnel to apply pressure is an undesirable cost factor.

To overcome the above deficiencies it has been suggested in the prior art to provide mechanical devices for applying pressure at the site of an arterial puncture. Exemplary prior art devices are disclosed in the U.S. Pat. Nos. 3,625,219, (Abrams); Semler, 3,779,249; McRae et al., 4,233,980; Sahota, 4,509,528 and Royse, 4,572,182. These prior art devices include pressure applying members which either are in the form of rigid, substantially planar disks or are in the form of inflatable pads. The use of rigid disks, which do not include any fluid in them, may not result in symmetrical pressure application, due to the rigidity of the pad and the normal inconsistency of the body tissue. Moreover, applying compression with a hard, non-yielding member may cause undue discomfort to a patient.

A disadvantage of the prior art devices employing inflatable pads is that the overall structure is generally complicated by the fact that an inflating system needs to be included as part of such devices. Moreover, inflatable pads may be subject to undesirable leakage, with possible complications.

When a clamp or other device is employed at the site of an arterial puncture it is highly desirable to monitor the rate of blood flow through the artery being compressed, as well as the magnitude of the applied pressure. In this manner an operator can determine the desired pressure for preventing an undesired decrease in the rate of blood flow through the artery.

The earlier-identified patent to Sahota, U.S. Pat. No. 4,509,528, discloses a hemostat which includes a blood flow sensor employing the Doppler effect fastened at an angle within a small recess in the bottom pressure-applying wall of the rigid pressure disk. In addition to the disadvantage of employing a rigid disk, as discussed above, the inclusion of an angled sensor in the bottom surface of the pad also is considered by applicant to be an undesirable arrangement. First, due to the location of the sensor on the bottom wall of the pad it may share in the bearing of the pressure exerted against the patient. This could possibly result in damage to the sensor. Second, due to the angular position of the sensor relative to the pressure-applying surface of the disk, it may be difficult to exactly locate the proper region for applying the pressure, particularly in overweight people wherein the distance between the pressure applying surface of the pad and the artery to be compressed is increased. Third, it may be cumbersome to clean and sterilize the pressure disk and Doppler center. Fourth, repeated use of objects that come into contact with human blood, such as the pressure disk in Doppler center disclosed in the Sahota '528 patent, is inadvisable, and use of disposable disks with a Doppler center may be excessively expensive.

It also is known to employ the Doppler effect to detect the pulse of a patient as part of a diagnostic system, as is exemplified by the system disclosed in the patent to Russell, U.S. Pat. No. 4,154,231. In this latter device a water-filled glass tube includes a rubber membrane at one end thereof for the purpose of detecting a pulse. This device has absolutely no therapeutic use, and is neither designed nor capable of exerting the high compression forces required to be employed in a manometric dressing of the type forming the subject matter of the present invention.

In Chen et al., U.S. Pat. No. 4,579,123 there is disclosed a device which is a stand-off unit for a transducer employed to image internal body parts. Chen et al. states that an important feature of this type of system is to avoid the need to apply a firm pressure to the device, since applying such a firm pressure would disturb the relative locations of structures in the body. Chen et al. also states that it is important that the liquid 23 not completely fill the cups 2 and 22.

Kawabuchi, U.S. Pat. No. 4,677,853 discloses an ultrasonic probe for use in an ultrasonic diagnosis device. This probe is capable of operating in a pulse-doppler mode or a continuous-doppler mode. The ultrasonic probe disclosed in the Kawabuchi '853 patent lacks the arrangement of elements forming the subject matter of the present invention.

OBJECTS OF THE INVENTION

It is a general object of this invention to provide an arterial manometric dressing which is of a simple and reliable design and construction.

It is a further object of this invention to provide an arterial manometric dressing employing a blood flow sensor which reliably locates the desired point of compression.

It is a further object of this invention to provide an arterial manometric dressing employing a blood flow sensor which will not be adversely affected by the force or pressure applied to an arterial site by a pressure member forming a part of the dressing.

It is a further object of this invention to provide an economical and disposable pressure-pad for use in an arterial manometric dressing. It is a further object of this invention to provide a unique, fluid-filled pressure pad for providing a desired uniform pressure to the arterial site.

It is a further object of this invention to provide an inexpensive and disposable fluid-filled pressure pad for isolating a blood flow sensor from the body surface to which pressure is being applied.

It is a further object of this invention to provide a manometric dressing which provides an indication of the pressure being applied to a patient.

SUMMARY OF THE INVENTION

The above and other object of the invention are achieved with an arterial manometric dressing including a unique pressure applying assembly having a pressure pad at a lower end thereof. A Doppler probe forms part of the pressure applying assembly and is in engagement with an upper wall means of the pressure pad. The pressure pad also includes a lower wall means spaced from the upper wall means for engaging a patient in a region in which pressure is to be applied to an artery, and a fluid for transmitting ultrasound signals to and from the Doppler probe is disposed between the upper and lower wall means. The pressure pad, in the most preferred embodiment of the invention, is easily separated from the remainder of the pressure-applying assembly, to thereby permit a new pressure pad to be utilized with each patient. This avoids the problem of contamination, which may result from the same pressure pad being utilized by more than one patient.

In the most preferred embodiment of this invention the upper and lower wall means of the pressure pad are part of a unitary, non-inflatable, non-expandable, pliable plastic material. Most preferably the upper wall of the unitary member has an upper substantially rigid member attached thereto, and this upper member has a peripheral surface therein defining a passageway for receiving one end of the Doppler probe.

In the most preferred embodiment of the invention the peripheral wall means defining the passageway through the upper rigid member of the pad is threaded to receive a threaded end of the Doppler probe.

In the most preferred embodiment of the invention the manometric dressing includes a vertically oriented pressure applying assembly having an outer tubular member and an inner tubular member telescoped within the outer tubular member, said outer tubular member having a pressure sensor therein for sensing pressure through the inner tubular member when a pressure applying pad of the dressing is placed into pressure engagement with a patient.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 3 is a sectional view taken along line 3—3 of FIG. 2; and

FIG. 4 is an isometric view of a pressure-applying pad in accordance with this invention.

DESCRIPTION OF THE PREFERRED EMBODIMENTS OF THE INVENTION

Figure 1:
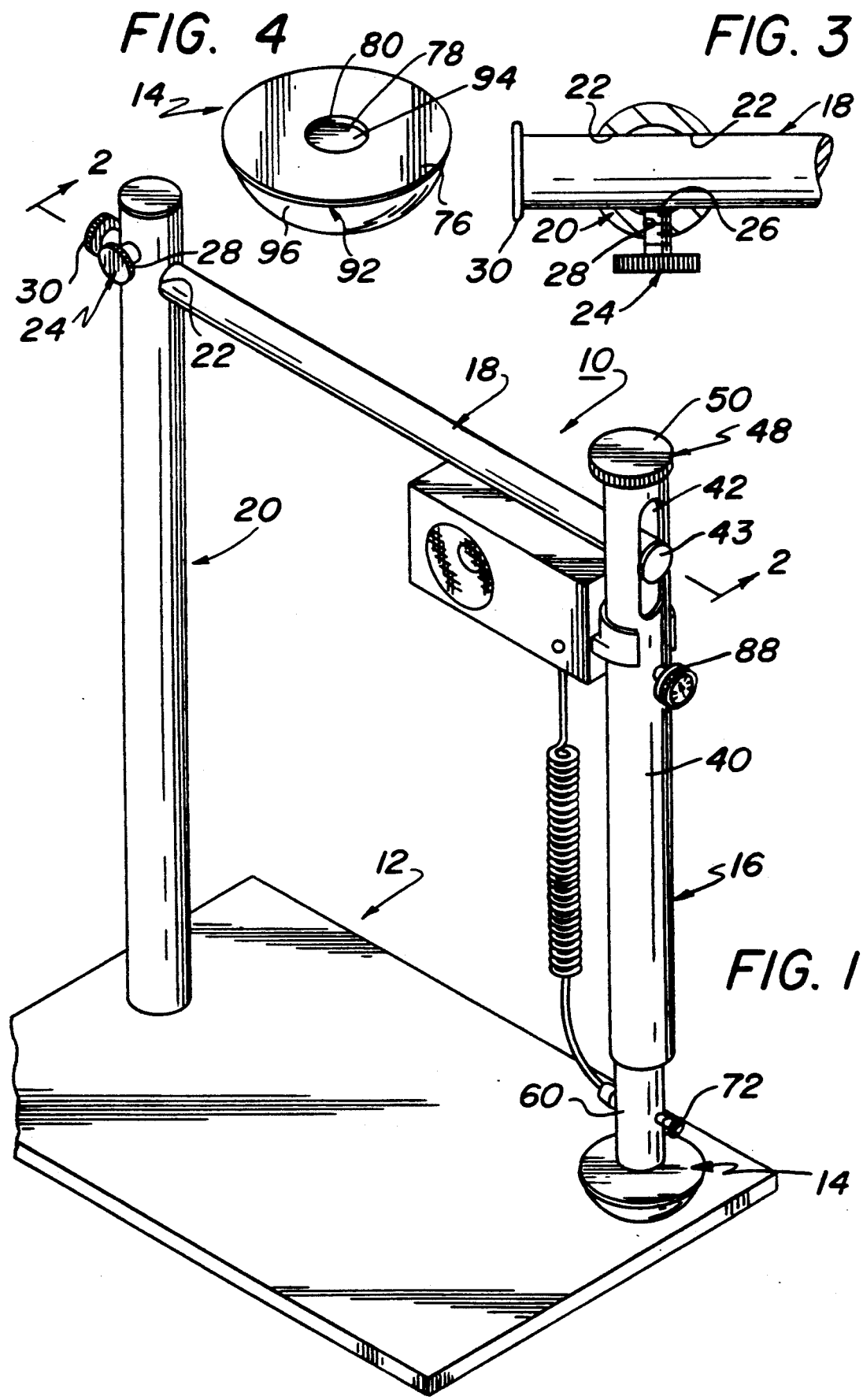
FIG. 1 is an isometric view of an arterial manometric dressing in accordance with this invention.

Referring now in greater detail to the various figures of the drawings wherein like reference characters refer to like parts, an arterial manometric dressing embodying the present invention is shown at 10 in FIG. 1. The device 10 basically comprises a supporting platform 12 upon which a portion of the body, e.g., a patient's groin or leg, is positioned to receive compressive forces applied through a fluid-filled, non-expandable, non-inflatable, pliable pressure pad 14 removably attached to a forearm assembly 16. The forearm assembly is movably connected to a horizontal support arm 18, which in turn is adjustably carried by a vertical column 20 secured to the platform 12.

When the dressing 10 is employed to apply compression at an arterial site to promote formation of a blood clot or thrombosis to close an arterial puncture, such as results from a catheterization procedure, the region of the person's body in which the puncture has been made is placed on the platform 12, and a compressive force is applied to that region through the pressure pad 14. As will be explained hereinafter, the arterial dressing 10 of this invention is capable of monitoring both pressure applied to the arterial site and the rate of blood flow through the artery in an extremely simple and reliable manner.

Referring specifically to FIGS. 1 and 3, the horizontal support arm 18 is slidably and rotatably received through diametrically opposed openings 22 in the vertical column 20, to thereby permit both axial and rotational adjustment of the pressure-applying pad 14. A screw clamp 24 including a clamping shoe 26 is employed to immobilize the arm 18 after is has been moved to properly position the pad (FIG. 3). Specifically, the screw clamp 24 is threaded into an opening 28 which is offset ninety degrees from the openings 22 to thereby permit the clamping shoe 26 to clampingly engage the periphery of the arm 18. A flange 30 is provided at one end of the arm 18 to prevent inadvertent axial movement of the arm out of the opposed openings 22 in the column 20.

Figure 2:
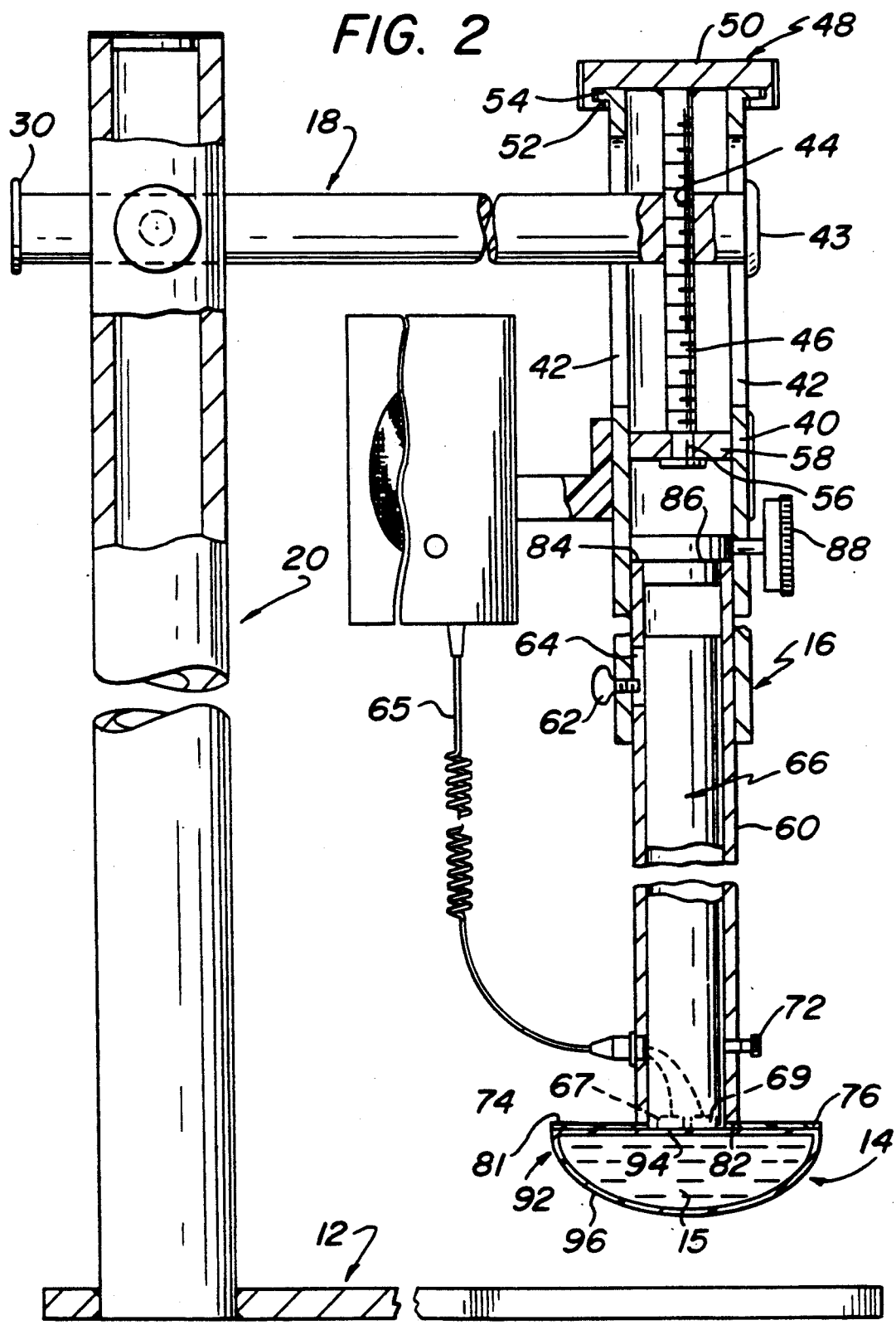
FIG. 2 is a sectional view taken along line 2—2 of FIG. 1.

Referring specifically to FIGS. 1 and 2, the forearm assembly 16 includes an outer tubular member 40 having diametrically opposed, vertically elongate slots 42 therein. The end of the arm 18 remote from flange 30 extends through the vertically elongate slots 42, and likewise includes a flange 43 to aid in maintaining the arm 18 in proper position relative to the forearm assembly 16.

As can be seen best in FIG. 2, a threaded passage 44 extends diametrically through the arm 18 for receiving the threaded shaft 46 of a rotatable adjustment member 48. The adjustment member 48 includes a rotatable head 50, to which the shaft 46 is attached, such as by welding. The head 50 includes an inturned annular flange 52 which underlies an outward annular flange 54 at the upper end of the tubular member 40, to thereby permit the head 50 to be rotated relative to the tube, but without separating from said tube. A lower, unthreaded section 56 of the shaft 46 is rotatably received within a bearing block 58 to further stabilize the rotatable adjusting member 48. It should be apparent that rotation of the adjustment member 48 in one direction will cause the forearm assembly 16 to move downwardly with respect to the horizontal arm 18, as viewed in FIG. 2, whereas rotation of the adjustment member 48 in the opposite direction will cause the forearm assembly 16 to move upwardly with respect to said horizontal arm.

Still referring to FIGS. 1 and 2, the forearm assembly 16 further includes an inner tubular member 60 slidably received in the outer tubular member 40. Although not shown in FIG. 2, there is a slight clearance between the inner and outer tubular members 60 and 40 to thereby prevent any significant frictional resistance to relative sliding movement between said inner and outer tubular members. In order to prevent the inner tubular member 60 from separating from the outer tubular member 40 a retaining pin member 62 is threaded into a passage in the wall of the outer member 40, and includes a section extending into the region of an elongate slot 64 provided in the wall of the inner member 60. As a result of this arrangement limited relative movement between the inner and outer tubular members can take place, but these latter members are prevented from separating from each other.

In accordance with a preferred feature of this invention the arterial manometric dressing 10 includes a Doppler unit 65. This unit includes a Doppler probe 66, a speaker unit 68 including the batteries (not shown) for providing power to the probe 66, and also including a rheostat-controlled, power/volume switch 71 thereon. The Doppler unit 65 is completed by an interconnecting cable 72 between the speaker unit 68 and the probe 66. As can be seen best in FIG. 2, the Doppler probe 66 is of a conventional design; including a sensor for detecting the flow of blood through a blood vessel. Specifically, the sensor comprises a transmitter 67 for transmitting ultrasound signals through the skin to a blood vessel and a receiver 69 in the form of a transducer for detecting the Doppler shift in the reflected ultrasound signal, which results from the movement of the red blood cells through the blood vessel. The Doppler shifted ultrasound signal is then analyzed in a conventional manner by a signal processor within the Doppler unit 65 to produce a sound signal that varies in pitch or volume in response to changes in blood flow. The sound signal generated through the use of the Doppler probe 66 is monitored through the speaker unit 68, with the volume of said speaker being set by the rheostat-controlled switch 71.

A Doppler unit having the above-described operational characteristics is manufactured by Imex Medical Systems, Inc. of Golden, Colorado, under its trademark Pocket-Dop II. This latter unit, with some modifications to its geometric shape and dimensions can be employed as the Doppler unit 65 in the present invention.

Still referring to FIG. 2, the Doppler probe 66 is axially adjustable within the interior of the tubular member 60, and is maintained in a desired, set position within the tubular member by a retention screw 72.

The lower end 74 of the Doppler probe 66 is provided with threads (not shown) for the purpose of establishing a removable, threaded connection with the pressure pad 14. Specifically, as is shown most clearly in FIG. 4, the pressure pad 14 includes an upper, rigid horizontal base member 76 having a central passageway 78 therein. This passageway has a threaded wall 80 for receiving the lower threaded end 74 of the Doppler probe. Once the connection is made between the Doppler probe 66 and the pad 14, the Doppler probe is moved in an upward direction within the inner tubular member 60 until upper surface 81 of the horizontal base member 76 engages lower surface 82 of the inner member 60. As a result of this arrangement, pressure applied through the pad 14 will be transmitted predominantly to the inner tubular member 60, rather than to the more delicate sensing and transmitting components of the Doppler probe 66.

As can be seen best in FIG. 2, the upper edge 84 of the inner tubular member 60 engages a pressure sensor 86 just prior to a compressive force being transmitted through the pressure pad 14, to thereby sense the pressure being applied to a patient. The sensor 86 is connected to a visually readable pressure gauge 88 to provide a visual read-out of the applied pressure.

Referring specifically to FIGS. 2 and 4, a unique feature of this invention resides in the fluid-filled non-expandable, non-inflatable, pliable pressure pad 14. In particular, the interior of the pad 14 is filled with a fluid 15 which is capable of transmitting ultrasound signals therethrough. The fluid can be water or a jelly-like material, if desired.

The pad 14 is a semi-spherical shaped member having an outer shell 92 formed of Silastic or other similar non-expandable, pliable plastic material which is capable of transmitting ultrasound signals therethrough. A flat upper wall 94 of the Silastic shell is secured to the substantially rigid horizontal base member 76 by a suitable adhesive composition (not shown). When the lower threaded end 74 of the Doppler probe 66 is threaded into the central passageway 78 of the base member 76, the sensor of the probe, which includes the transmitting and receiving elements, will be in engagement with Silastic upper wall 94 to thereby provide reliable signal transmission both to and from the artery under compression. A small amount of jelly that transmits ultrasound may be placed on top of upper wall 94 to obtain air-free contact between the sensor of the Doppler probe 66 and the pad 14. The hemispherical face 96 of the outer shell 92 is employed to directly engage the skin of the patient and is deformable, i.e., pliable, to apply a substantially uniform pressure to the desired arterial site.

As a result of the above arrangement the sensor of the Doppler probe 60 is separated from a patient's skin by the pressure pad 14. This overcomes the disadvantages associated with the use of a pressure pad employing a sensor on the lower pressure engaging surface, as is disclosed in the earlier-discussed Sahota '528 patent. Moreover, the sensor of the probe 60 is not angled relative to the axis of movement of the forearm assembly 16, and also is aligned with the center of the pressure pad, thereby providing and detecting signals which reliably locate the artery under compression for determining the rate of blood flow through said artery. Moreover, due to the fact that the hemispherical face 96 of the pad 14 is deformable, it will tend to conform to the non-homogeneous consistency of the human tissue, against which the compressive force is exerted.

Without further elaboration the foregoing will so fully illustrate my invention that others may, by applying current or future knowledge, adopt the same for use under various conditions of service.

What is claimed is:

1. An arterial manometric dressing including a pressure applying assembly having a Doppler probe and a pressure pad, said Doppler probe having a sensor means at a lower end thereof for detecting the flow of blood through a blood vessel, said pressure pad being at a lower end of the assembly, characterized in that said pressure pad includes a pliable shell having an interior compartment, a fluid for transmitting ultrasonic signals therethrough, to and from said Doppler probe, fililng said interior compartment, said shell including an upper wall means for engaging the lower end the Doppler probe when sid probe is attached to said pressure pad, and a lower wall measn for engaging a patient in a region and for applying pressure to an underlying artery, said pressure pad including a substantially rigid member secured to the upper wall means of the pad and including a threaded peripheral surface providing a threaded passageway therethrough, said passageway communicating with the upper wall means of the pad, said lower end of the Doppler probe being threaded for threadably engaging the threads on the peripheral surface defining the passageway to thereby removably attach the pad to the Doppler probe.

2. The arterial manometric dressing of claim 1 characterized in that the shell is a unitary, pliable plastic member.

3. A pressure pad for applying pressure to a patient in a region of an artery, said pressure pad including a non-expandable, non-inflatable and pliable shell having an interior compartment, a fluid for transmitting ultrasonic signals therethrough filling said interior compartment, said shell including an upper wall means for engaging a lower end of a Doppler probe when said probe is attached to said pressure pad, said lower end of the probe including a sensor means for detecting the flow of blood through a blood vessel, said shell further including a lower wall means for engaging a patient in a region and for applying pressure to an underlying artery, sid pressure pad including a substantially rigid member secured to the upper wall means of the pad and including a threaded peripheral surface providing a threaded passageway therethrough, said passageway communicating with the upper wall means of the pad and being adapted to receive said lower end of the Doppler probe herein with the threads of the passageway securing the Doppler probe to said pad with the lower end of said Doppler probe in engagement with the upper wall means of the pad.

4. The pressure pad of claim 3 characterized in that said passageway through the upper member is centrally located in said upper member.

5. An arterial manometric dressing including a vertical support member, a horizontal support member having opposed ends, one of said opposed ends being movably supported by the vertical support member and the other of said opposed ends movably supporting a vertically oriented pressure applying assembly, said pressure applying assembly including an outer tubular member, an inner tubular member telescoped within the outer tubular member and movable relative to said outer tubular member, a Doppler probe movably mounted within said inner tubular member and means for maintaining said probe in a fixed position relative to said inner tubular member, said probe having a lower end extending outwardly of a downstream end of said inner tubular member, said lower end including a sensor measn for detecting the flow of blood through a blood vessel, and a pressure pad attached to said probe, said pressure pad including a pliable shell providing an interior compartment, a fluid for transmitting ultrasonic signals therethrough, to and from sid Doppler probe, filling said interior compartment, said shell including an upper wall means for engaging the lower end of the Doppler probe, filling said interior compartment, said shell including an upper wall means for engaging the lower end of the Doppler probe when said probe is attached to said pad, and a lower wall means for engaging a patient in a region and for applying pressure to an underlying artery, said pressure pad including a substantially rigid member secured to the upper wall means of the pad and including a peripheral surface providing a passageway therethrough, said passageway communicating with the upper wall means of the pad, said lower end of the Doppler probe being received within the passageway and being attached to the peripheral surface providing said passageway, said substantially rigid member having an upper surface in engagement with the downstream end of said inner tubular member when pressure is being applied to the artery.

6. The arterial manometric dressing of claim 5, characterized in that the outer tubular member of the pressure applying assembly including a pressure sensor means therein, said inner tubular member having an edge opposed to said one end for engaging said pressure sensor and applying a force thereto when said inner tubular member is biased by the engagement of the substantially rigid member of the pressure pad with said one end of said inner tubular member as pressure is being applied to the artery through said pressure pad.

7. The arterial manometric dressing of claim 6, characterized in that a pressure gauge is connected to said pressure sensor to provide a visual read-out of the pressure applied to the artery through the pressure pad.

8. An arterial manometric dressing including a vertical support member, a horizontal support member having opposed ends, one of said opposed ends being movably supported by the vertical support member and the other of said opposed ends movably supporting a vertically oriented pressure applying assembly, said pressure applying assembly including an outer tubular member, an inner tubular member telescoped within the outer tubular member and movable relative to said outer tubular member, said outer tubular member having a pressure sensor therein, a Doppler probe movably mounted within said inner tubular member and means for maintaining said probe in a fixed position relative to said inner tubular member, said probe having a lower end extending outwardly of one end of said inner tubular member, said lower end including a sensor means for detecting the flow of blood through a blood vessel, said pressure pad including a pliable shell providing an interior compartment, a fluid for transmitting ultrasonic signals therethrough, to and from said Doppler probe, filling said interior compartment, said shell including an upper wall means for engaging the lower end of the Doppler probe when said probe is attached to said pad, and a lower wall means for engaging a patient in a region and for applying pressure to an underlying artery, said pressure pad including an upper surface for in engagement with said one end of said inner tubular member when pressure is being applied to the artery for biasing said inner tubular member, said inner tubular member having an edge opposed to said one for engaging said pressure sensor and applying a force thereto when pressure is being applied to the artery through said pressure pad.

9. The arterial manometric dressing of claim 8, characterized in that a pressure gauge is connected to said pressure sensor to provide a visual read-out of the pressure applied to the artery through the pressure pad.

* * * * *